United States Patent [19]
Gittings

[11] Patent Number: 5,484,416
[45] Date of Patent: Jan. 16, 1996

[54] COAXIAL CABLE VASCULAR ACCESS SYSTEM FOR USE IN VARIOUS NEEDLES

[75] Inventor: Darin Gittings, Sunnyvale, Calif.

[73] Assignee: Advanced Cardiovascular Systems, Inc., Santa Clara, Calif.

[21] Appl. No.: 102,607

[22] Filed: Aug. 5, 1993

[51] Int. Cl.⁶ .................................................. A61M 5/00
[52] U.S. Cl. .............................................................. 604/164
[58] Field of Search ................................ 604/164, 19–22, 604/53; 128/662.06–662.05; 601/2; 606/39, 45, 32; 607/96, 113, 115, 116, 138, 156, 101, 102

[56] References Cited

U.S. PATENT DOCUMENTS

| 4,887,606 | 12/1989 | Yoek et al. | 128/662.06 |
|---|---|---|---|
| 4,935,008 | 6/1990 | Lewis, Jr. | 604/164 |
| 5,156,596 | 10/1992 | Balbierz et al. | 604/164 |
| 5,259,385 | 11/1993 | Miller et al. | 128/662.05 |
| 5,290,244 | 3/1994 | Moonka | 604/164 |

*Primary Examiner*—C. Fred Rosenbaum
*Assistant Examiner*—Manuel Mendez
*Attorney, Agent, or Firm*—Dykema Gossett

[57] ABSTRACT

A vascular access system for accurately locating body structures, such as blood vessels within a patient includes a flexible probe for applying Doppler ultrasonic techniques that has a relatively adjustable length relative to a needle assembly. The flexible probe has a coaxial cable design that includes a piezoelectric element at a proximal end of the probe. The piezoelectric element is used for emitting ultrasonic signals and for receiving ultrasonic signals that are reflected off of various body structures within a patient. The intensity of the reflective ultrasonic signals is used to determine the location of a preselected body structure. The flexible probe is adaptable for use within a variety of needles for a variety of applications.

22 Claims, 1 Drawing Sheet

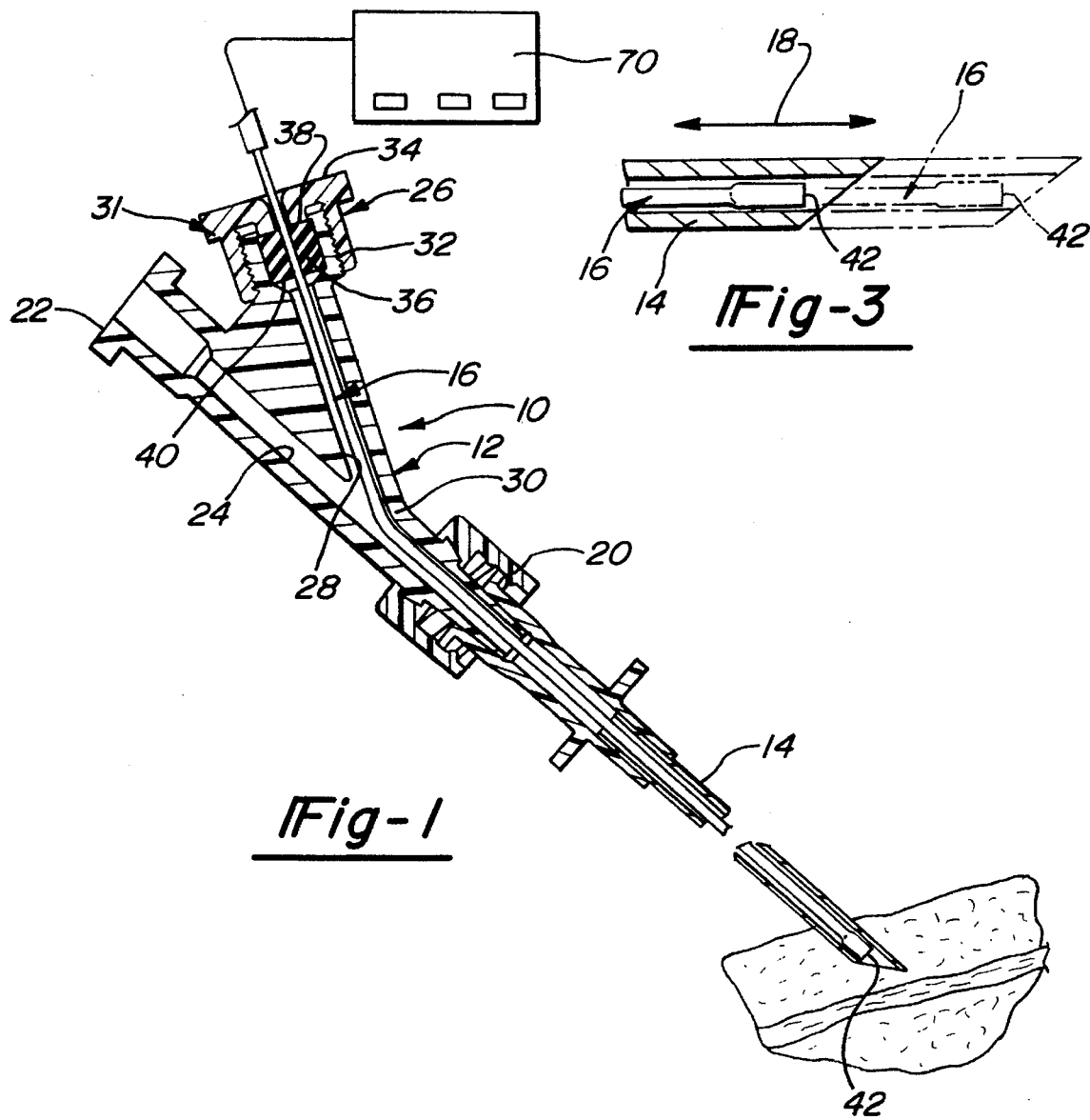
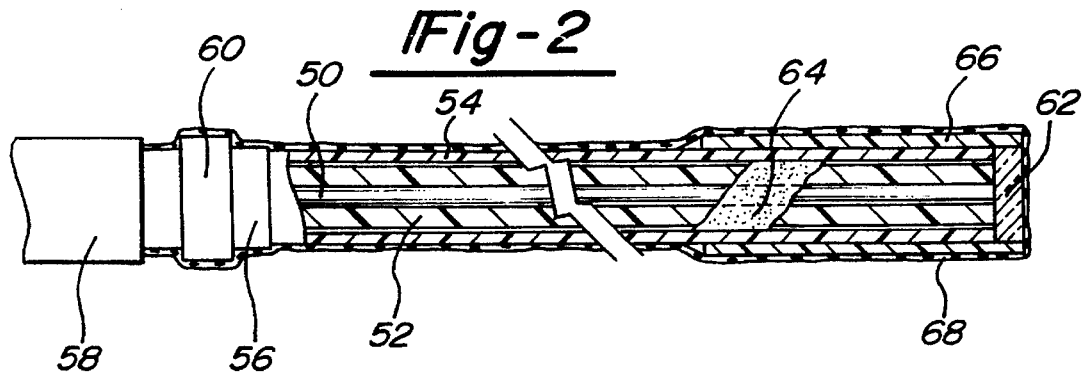

COAXIAL CABLE VASCULAR ACCESS SYSTEM FOR USE IN VARIOUS NEEDLES

BACKGROUND OF THE INVENTION

This invention generally relates to a vascular access system for locating structures such as blood vessels within a patient's body. More specifically, this invention relates to a flexible coaxial cable probe for locating body structures within a patient using Doppler technology that provides a relatively adjustable length so that it is adaptable to a variety of needles.

The insertion of arterial and venous catheters for various purposes including angiography can prove difficult for medical professionals. Locating and penetrating arteries and veins is especially difficult when dealing with patients who are obese or present unusual anatomy. When a medical professional has difficulty locating an artery or vein, the patient is subjected to increased discomfort. Various devices improve accuracy in locating vessels within a patient's body and, thereby decrease the amount of discomfort a patient must endure. One such attempt includes the use of Doppler ultrasound technology.

The potential utility of Doppler ultrasound for accurately guiding a needle into a vessel has been recognized. Certain applications utilize the transmission of ultrasonic waves through the needle and the reception of ultrasonic echoes by a separate transducer located on the body of the patient separated from the syringe an needle. Such applications can give erroneous signals, particularly when the needle is engaging the blood vessel or immediately before penetrating the blood vessel. An improvement over such applications includes a transducer insert positioned within a hollow needle that has an ultrasonic transducer at one end for transmitting and receiving ultrasonic waves within the sharpened end of the needle. However, the fixed construction of the latter transducers typically limits their application to a specific size (length) of needle.

When the transducer probe has a rigid body for a portion of its length, this rigid body portion is typically located within the needle and a portion of a needle housing. A typical needle housing for a probe of this type includes a side arm through which the transducer is electrically coupled to a power source and/or a device for interpreting information gained through the transducer. Such side arms are typically oriented at an acute angle bend relative to the axis of the needle. Because the probe body is rigid, it cannot be retracted around the bend and back through the side arm. Thus, a coaxial cable has been connected to the rigid body probe to properly electrically couple the transducer to the power source. The coaxial cable is used for its ability to be bent at the turn between the longitudinal axis of the needle housing and the side arm. However, the cable attachment to the rigid body probe necessarily includes a larger diameter due to the soldering and shrink tubing needed to make the connection. This larger diameter connection prohibits the probe from advancing down into the needle while the rigidity of the probe body in the needle does not allow the probe to retract into the side arm. Therefore, such probes inherently have a fixed length relative to the needle and/or needle housing.

Nevertheless, it is desirable to have a transducer probe for utilizing Doppler ultrasound techniques that has a relatively adjustable length within a needle and needle housing. When a probe has a fixed length relative to a needle, the number of needles that can be used with such a probe is normally limited to one. This is because the location of the probe near the distal end of the needle is crucial to proper functioning and use of Doppler ultrasound techniques. Thus, a probe having a relatively adjustable length would have the advantage of being adaptable to a variety of needle sizes (lengths). Further, such a probe inherently would provide cost efficiencies as it is usable with a variety of needles for a variety of applications.

SUMMARY OF THE INVENTION

This invention includes an adjustable length probe for use within a needle assembly for sensing the position of body structures, such as blood vessels, within a patient by using Doppler ultrasound techniques. An entirely coaxial probe has been designed according to this invention which includes a center conductor surrounded by a dielectric tube. Shielding means surrounds a portion of the dielectric tube such that a predetermined length of the dielectric tube extends beyond the shielding means. The exposed dielectric tube can be made any length to accommodate various needle lengths. A jacket covers a portion of the shielding means such that a predetermined length of the shielding means extends beyond the jacket. The portion of the shielding means that extends beyond the jacket is anchored to the dielectric tube by a means for anchoring. A piezoelectric element is connected to a proximal end of the dielectric tube. Lastly, means for preventing electrical shorts across the piezoeletric element and means for electrically coupling the piezoelectric element to the shielding means are provided.

A probe constructed in accordance with this invention includes several advantages compared to prior attempts at applying Doppler ultrasound technology to vessel location within a patient's body. The inventive probe is adjustable and flexible along its entire length. As such, the inventive probe can be used for various applications in a variety of needles, as it has an adjustable length relative to a needle assembly.

When a needle is appropriately connected to a needle housing having a side arm, the inventive probe can be inserted through the channel in the side arm and housing and into and through the needle to an appropriate position near the proximal end of the needle. The flexibility of the inventive probe allows the probe to bend around an angled bend between any channels in a needle housing. Typically, side arms provided on such needle housings are at an angle of 30 degrees relative to the axis of the needle. The inventive probe has no difficulty negotiating the turn from a 30 degree bend and can therefore be moved axially within the housing and the needle into an appropriate position.

A needle housing in accordance with the present invention preferably includes a locking means at the opening of the side arm where the flexible probe is inserted. In a presently preferred embodiment, the locking means includes an internally threaded member that engages an externally threaded end near the opening on the housing where the probe is inserted. Also included, is a pressure means that responsively exerts pressure radially upon the probe when the internally threaded member is adjusted relative to the housing. The pressure means, therefore, holds the probe temporarily at a preselected fixed axial position relative to the housing. Such locking mechanisms are commonly known as Toughy-Borst Locking Mechanisms.

These and other features and advantages of this invention will become apparent to one skilled in the art from the following description, appended claims and drawings; the latter being briefly described as follows.

BRIEF DESCRIPTION OF THE DRAWINGS

FIG. 1 is a partial cross-sectional view of a flexible probe in a needle housing.

FIG. 2 is a partial cross-sectional view of a coaxial cable forming a flexible probe.

FIG. 3 illustrates the adjustability feature of the probe.

DETAILED DESCRIPTION OF THE PREFERRED EMBODIMENT

FIG. 1 illustrates needle assembly 10 including housing 12, needle 14 and flexible probe 16. Flexible probe 16 has an adjustable length relative to housing 12 and needle 14 as shown generally by direction arrow 18 in FIG. 3 as will be more fully described below.

Housing 12 includes first end 20 adapted to be connected to a variety of needles. Second end 22 is axially opposite first end 20 and preferably coaxial with first end 20. Second end 22 is adapted to be connected to a syringe, for example. Housing 12 includes first channel 24 defined between first end 20 and second end 22. Third end 26 is adapted to receive flexible probe 16. A second channel 28 is defined between third end 26 and a medial location along first channel 24 that defines a bend 30. As illustrated, when in use, flexible probe 16 is axially movable through second channel 28 and a portion of first channel 24 and needle 14 such that flexible probe 16 bends around bend 30. First channel 24 and second channel 28 typically have a relative angle of orientation of approximately 30 degrees.

Third end 26 preferably includes locking means 31. Locking means 31 includes external threads 32 which can be formed on third end 26 of housing 12. Internally threaded adjustable member 34 is received over external threads 32. Pressure means 36 is contacted by surface 38 on adjustable member 34. Pressure means 36 is received in the portion of housing 12 indicated at 40 such that the relative adjustment of member 34 along external threads 32 causes surface 38 to bear against and apply an axial pressure on pressure means 36. Such axial pressure compresses pressure means 36 in such manner that pressure means 36 exerts a radially compressive force on flexible probe 16. In this manner, flexible probe 16 is temporarily held axially fixed relative to housing 12. Pressure means 36 also acts as a seal against leakage from the third end 26.

Flexible probe 16 can be axially slid through housing 12 and needle 14 to an appropriate position such that a proximal end 42 of flexible probe 16 is appropriately positioned within needle 14. Locking means 31 can then be appropriately adjusted to maintain flexible probe 16 in this preselected position.

Housing 12 is preferably made of a clear, lightweight plastic material for easy manipulation and to enable a medical professional to observe the passage of medication or blood through first channel 24 when appropriate.

FIG. 2 shows, in partial cross-sectional view, a preferred embodiment of flexible probe 16. A solid center conductor 50 is surrounded by a dielectric tube 52. In a preferred embodiment, the conductor is surrounded by a Teflon dielectric tube, which provides improved noise suppression during operation. Conductor 50 can be composed of copper, silver, or silver-plated copper. A means for enhancing bondability 54 is coextruded over dielectric tube 52. In a preferred embodiment, means 54 is a thin layer of nylon, which is capable of being adhered to by conductive adhesive. Shielding means 56 covers a portion of dielectric tube 52. Shielding means 56 is preferably a braid or a foil wrap over a drain wire. A silicon, Teflon or other type of jacket 58 completes a portion of the probe-cable assembly. Jacket 58 and shielding means 56 are preferably stripped off the dielectric tube 52, leaving ¼ of an inch of the shielding means exposed. Anchoring means 60 anchors shielding means 56 to dielectric tube 52. Anchoring means 60 can be a conductive ring or hollow cylindrical crimp. The exposed length of dielectric tube 52 extending beyond shielding means 56 can be any preselected length necessary, depending on the maximum length of needle with which the probe is intended for use.

The proximal end of flexible probe 16 includes piezoelectric element 62 which is affixed to dielectric tube 52 by connecting means 64. Connecting means 64 is preferably a conductive adhesive. Piezoelectric element 62 and connecting means 64 are encapsulated in a polyimide sleeve 66 that serves as means for preventing electrical shorts across piezoelectric element 62. Polyimide sleeve 66 also provides the advantage of preserving the mechanical integrity of the proximal end 42 of flexible probe 16. A conductive layer 68 surrounds all portions of flexible probe 16 that are not covered by jacket 58. Conductive layer 68 serves as a means for electrically coupling piezoelectric element 62 to shielding means 56. In the preferred embodiment, conductive layer 68 is composed of a conductive adhesive.

When needle 14 is inserted within a patient's body as shown in FIG. 1, for example to make an arterial injection, flexible probe 16 assists the medical professional in locating the artery to receive the injection. Piezoelectric element 62 emits ultrasonic signals that emanate outwardly from the end of needle 14. These ultrasonic signals are reflected off of body structures such as blood vessels and the reflective signals are detected by piezoelectric element 62. It is well known, that the phenomenon known as the Doppler effect can be utilized to accurately locate body structures such as blood vessels. The intensity of the reflected ultrasonic signals will increase as the proximal end of needle 14 approaches the preselected artery. By manipulating needle assembly 10 such that needle 14 moves slightly arcuately within the patient, a user or medical professional can determine whether the needle 14 is directly approaching the preselected artery or vein based upon the information discernible from the reflected ultrasonic signals received by piezoelectric element 62.

The inventive probe can be coupled with conventional power supplies such as 70 to cause piezoelectric element 62 to emit ultrasonic signals and conventional electronics for interpreting the information gained from the reflected ultrasonic signals. An example of a device which is known to operate and function in the manner just described is disclosed in U.S. Pat. No. 4,887,606, which is incorporated by reference herein.

The inventive probe has the distinct advantage of being adaptable for use within a variety of needles and for a variety of applications. This flexibility and adjustability provides economies and efficiencies in manufacturing and in actual use of a probe. For example, the coaxial conductor and tube assembly forming part of probe 16 can be wound onto a reel and removed therefrom depending on the length of probe desired. Further, the inventive probe can be efficiently used with a variety of catheters. For example, a catheter assembly could be appropriately connected to second end 22 of housing 12. After the proper artery is located by using probe 16 and the appropriate length of the needle is inserted into the artery, probe 16 can be moved axially and retracted out of needle 14 and first channel 24 so the catheter can then be inserted into the artery through the needle.

The foregoing description is illustrative rather than limiting in nature. A preferred embodiment has been disclosed to enable one skilled in the art to practice this invention. Variations and modifications are possible that do not depart from the purview and spirit of this invention; the scope of which is limited only by the appended claims.

What is claimed is:

1. A vascular access system for accurately locating body structures, such as blood vessels, within a patient, comprising:

a housing having a first opening adapted to be connected to a needle, a second opening axially opposite said first opening adapted to be connected to a syringe, said housing having a first channel with ends at said first and second openings, respectively, said housing having a third opening and a second channel beginning at said third opening and terminating at a medial location in said first channel, said second channel intersecting said first channel at said medial location; and a flexible, axially movable, and adjustable probe partially disposed within said housing such that said probe extends through said third opening, said second channel, said medial location, a portion of said first channel and said first opening, respectively, such that a portion of said probe extends beyond said housing at said first and third openings, respectively, said probe being axially movable within said first and second channels such that said probe has an adjustable length relative to said housing, said probe being adapted to be axially movable within a needle that is properly attached to said housing first opening, said probe comprising means at one end for emitting ultrasonic signals and for receiving ultrasonic signals that are reflected off of body structures, whereby a user can interpret the reflected signals to thereby locate preselected body structures within a patient.

2. The system of claim 1 wherein said third housing opening comprises locking means for temporarily locking said probe in a preselected position relative to said housing to thereby maintain said probe axially fixed within said housing such that the portion of said probe that extends beyond said first opening has a predetermined temporarily fixed length relative to said housing.

3. The system of claim 2 wherein said locking means comprises a first externally threaded member, a second internally threaded member adjustably connected to said first member and a pressure means adapted to receive said probe such that the relative adjustment of said first and second members causes said pressure means to radially bear against said probe thereby rendering said probe temporarily axially immovable relative to said housing.

4. The system of claim 1 wherein said probe comprises a coaxial cable that has a generally consistent flexibility along the length of said probe.

5. The system of claim 4 wherein said probe comprises:

a conductor surrounded by a dielectric tube;

shielding means surrounding a portion of said dielectric tube such that a proximal end and a predetermined length of said dielectric tube extends beyond said shielding means;

a jacket covering a portion of said shielding means such that a predetermined length of said shielding means extends beyond said jacket, said jacket being distal from said dielectric tube proximal end;

means for anchoring said extending length of said shielding means to said dielectric tube;

a piezoelectric element disposed adjacent said dielectric tube proximal end;

means for connecting said piezoelectric element to said dielectric tube;

means for preventing electrical shorts across said piezoelectric element; and means for electrically coupling said piezoelectric element to said shielding means.

6. A probe for use within a needle assembly for sensing the position of body structures, such as blood vessels, within a patient using ultrasonic signals, comprising:

a conductor having a longitudinal length and a diameter that is much smaller than said length;

a dielectric surrounding said conductor;

shielding means surrounding a portion of said dielectric such that a proximal end and a predetermined length of said dielectric extends beyond said shielding means;

a jacket covering a portion of said shielding means such that a predetermined length of said shielding means extends beyond said jacket, said extending length of said shielding means being toward said dielectric proximal end;

means for anchoring said extending length of said shielding means to said dielectric;

a piezoelectric element disposed adjacent said dielectric proximal end;

means for connecting said piezoelectric element to said dielectric;

means for preventing electrical shorts across said piezoelectric element; and means electrically coupling said piezoelectric element to said shielding means.

7. The probe of claim 6 further comprising means for enhancing bondability between said dielectric and said shielding means.

8. The probe of claim 7 wherein said enhancing means comprises a thin layer of nylon coextruded over said dielectric.

9. The probe of claim 6 wherein said conductor comprises a flexible solid single strand of copper.

10. The probe of claim 6 wherein said conductor comprises a flexible solid single strand of silver.

11. The probe of claim 6 wherein said conductor comprises a flexible solid single strand of silver plated copper.

12. The probe of claim 6 wherein said dielectric comprises a Teflon tube.

13. The probe of claim 6 wherein said shielding means comprises a foil braid over a drain wire.

14. The probe of claim 6 wherein said shielding means comprises a foil wrap over a drain wire.

15. The probe of claim 6 wherein said jacket comprises a silicone sheath.

16. The probe of claim 6 wherein said jacket comprises a Teflon sheath.

17. The probe of claim 6 wherein said anchoring means comprises a nonconductive generally cylindrical crimp.

18. The probe of claim 6 wherein said connecting means comprises a conductive adhesive.

19. The probe of claim 6 wherein said means for preventing electrical shorts across said piezoelectric element comprises a polyimide sleeve that effectively encapsulates said piezoelectric element and said connecting means.

20. The probe of claim 6 wherein said means for electrically coupling said piezoelectric element to said shielding means comprises a coating of conductive material effectively surrounding all portions of said probe extending beyond said jacket, said coating effectively encapsulating said proximal end of said probe.

21. The probe of claim 6 wherein said means for electrically coupling said piezoelectric element to said shielding means comprises a conductive adhesive effectively surrounding all portions of said probe extending beyond said jacket, said conductive adhesive effectively encapsulating said proximal end of said probe.

22. A vascular access system comprising:
- a housing adapted to be connected to a plurality of hollow needles having varying lengths, said housing having a first channel in communication with a selected needle and a second channel connected to said first channel at a bend portion,
- a flexible, axially movable, and adjustable ultrasonic probe assembly adjustably movable through said second channel, through said bend portion, and into said selected needle said probe comprising a means at one end for emitting and receiving ultrasonic signals that are reflected of body structures such that said probe has an adjustable length within said selected needle; and
- means for temporarily securing said flexible probe at a predetermined position within said selected needle.

* * * * *